United States Patent
Kenzume et al.

(10) Patent No.: US 9,766,058 B2
(45) Date of Patent: Sep. 19, 2017

(54) DISTANCE MEASUREMENT SYSTEM AND DISTANCE MEASUREMENT METHOD

(71) Applicant: THE CHUGOKU ELECTRIC POWER CO., INC., Hiroshima (JP)

(72) Inventors: Tatsuya Kenzume, Hiroshima (JP); Hidetaka Nishida, Hiroshima (JP); Hideo Matsumura, Hiroshima (JP); Daisuke Arakawa, Hiroshima (JP)

(73) Assignee: THE CHUGOKU ELECTRIC POWER CO., INC., Hiroshima (JP)

( * ) Notice: Subject to any disclaimer, the term of this patent is extended or adjusted under 35 U.S.C. 154(b) by 0 days.

(21) Appl. No.: 14/763,039

(22) PCT Filed: Jan. 25, 2013

(86) PCT No.: PCT/JP2013/051647
§ 371 (c)(1),
(2) Date: Sep. 15, 2015

(87) PCT Pub. No.: WO2014/115315
PCT Pub. Date: Jul. 31, 2014

(65) Prior Publication Data
US 2016/0054445 A1    Feb. 25, 2016

(51) Int. Cl.
*G01B 11/14* (2006.01)
*G01C 3/00* (2006.01)
(Continued)

(52) U.S. Cl.
CPC ............ *G01B 11/14* (2013.01); *G01B 11/026* (2013.01); *G01B 11/16* (2013.01); *G01C 3/00* (2013.01);
(Continued)

(58) Field of Classification Search
CPC ........ G01S 17/08; G01S 17/88; G01S 17/488; G01S 7/481; G02B 21/02; G02B 21/16;
(Continued)

(56) References Cited

U.S. PATENT DOCUMENTS 4,305,299 A * 12/1981 Serata .................. G01B 7/24
                                              73/779
4,584,676 A *  4/1986 Newman .............. G01B 17/00
                                              367/108
(Continued)

FOREIGN PATENT DOCUMENTS

CN    201886153 U    6/2011
DE    102008048574 A1  3/2010
(Continued)

OTHER PUBLICATIONS

Yakushev, P.N., "Creep Rate Measurement with Laser Interferometer," 2009, Optical Memory and Neural Networks (Information Optics), vol. 18, No. 4, pp. 328-336.*
(Continued)

Primary Examiner — Gordon J Stock, Jr.
(74) Attorney, Agent, or Firm — Osha Liang LLP

(57) ABSTRACT

A distance measuring system includes: a reference member configured to be provided on a surface of a first pipe made of metal, the reference member serving as a reference for distance measurement; an attachment member provided on a surface of a second pipe, made of metal, connected with the first pipe through a weld; a distance sensor configured to be attached to the attachment member, to measure a distance to the reference member; and a measuring unit configured to measure the distance based on an output from the distance sensor.

9 Claims, 5 Drawing Sheets

(51) Int. Cl.
*G01N 21/88* (2006.01)
*G01N 17/00* (2006.01)
*G01B 11/16* (2006.01)
*G01B 11/02* (2006.01)
*G01B 7/02* (2006.01)
*G01B 7/14* (2006.01)
*G01S 17/08* (2006.01)
*G01S 17/88* (2006.01)

(52) U.S. Cl.
CPC ........... *G01N 17/006* (2013.01); *G01N 21/88* (2013.01); *G01B 7/023* (2013.01); *G01B 7/14* (2013.01); *G01S 17/08* (2013.01); *G01S 17/88* (2013.01)

(58) Field of Classification Search
CPC .... G02B 21/06; G02B 21/065; G02B 21/085; G02B 21/32; G02B 21/321; G01N 2021/1731; G01N 17/00; G01N 17/006; G01N 3/56; G01N 3/60; G01N 21/55; G01N 21/952; G01N 21/88; G01N 21/95; G01B 11/02; G01B 11/026; G01B 11/046; G01B 11/06; G01B 11/0616; G01B 11/0683; G01B 11/0691; G01B 11/16; G01B 15/02; G01B 15/06; G01B 5/14; G01B 7/023; G01B 7/14; G01B 7/16; G01B 7/17; G01B 7/20; G01B 7/22; G01B 7/24; G01B 11/04; G01B 11/043; G01B 11/14; G01C 3/00; G01C 3/08; G01C 3/12; G01C 3/10; G01C 3/22; G01C 3/24; G01C 3/26; G01M 3/00; G01M 3/38; G01L 315/02; G01L 315/06

See application file for complete search history.

(56) References Cited

U.S. PATENT DOCUMENTS

| | | | | |
|---|---|---|---|---|
| 4,671,654 A | * | 6/1987 | Miyahara | G01C 15/002 348/142 |
| 4,701,869 A | * | 10/1987 | Callegari, Sr. | G01B 11/02 702/158 |
| 5,035,143 A | * | 7/1991 | Latimer | G01N 29/041 367/127 |
| 5,084,980 A | * | 2/1992 | Skopec | E21B 25/16 33/228 |
| 5,172,587 A | * | 12/1992 | Long | G01N 3/08 73/784 |
| 6,332,361 B1 | * | 12/2001 | Yamada | G01N 29/11 73/598 |
| 6,606,910 B1 | * | 8/2003 | Nishimura | G01N 29/069 73/599 |
| 6,784,986 B2 | | 8/2004 | Lysen et al. | |
| 6,935,552 B2 | * | 8/2005 | Komai | G01N 23/2251 228/103 |
| 7,042,555 B1 | * | 5/2006 | Lawson | G01C 15/002 356/138 |
| 7,565,252 B2 | * | 7/2009 | Kim | G01N 29/075 702/35 |
| 8,186,875 B2 | * | 5/2012 | Tognarelli | G01N 3/18 374/46 |
| 9,074,871 B1 | * | 7/2015 | Lubeck | G01B 11/026 |
| 9,453,727 B1 | * | 9/2016 | Bruck | G01N 23/02 |
| 2001/0054317 A1 | * | 12/2001 | Arms | G01B 7/24 73/786 |

FOREIGN PATENT DOCUMENTS

| | | | | |
|---|---|---|---|---|
| GB | 2429783 A | * | 3/2007 | ............... B61K 9/08 |
| JP | 63-030756 A | | 2/1988 | |
| JP | 07-055454 A | | 3/1995 | |
| JP | 2000171211 A | * | 6/2000 | |
| JP | 2004-61300 A | | 2/2004 | |
| JP | 2008-122345 A | | 5/2008 | |
| JP | 2008-290182 A | | 12/2008 | |
| JP | 2009-20075 A | | 1/2009 | |
| JP | 2012-000659 A | | 1/2012 | |
| JP | 2013019758 A | * | 1/2013 | |
| WO | WO 2015136652 A1 | * | 9/2015 | ........... G01B 21/047 |

OTHER PUBLICATIONS

Notification of Transmittal of Translation of the International Preliminary Report of Patentability for corresponding International Application No. # PCT/JP2013/051647, mailed Aug. 6, 2015 (1 page).
International Preliminary Report on Patentability for corresponding International Application No. # PCT/JP2013/051647, issued Jul. 28, 2015 (1 pages).
English Translation of Written Opinion issued in corresponding PCT Application No. PCT/JP2013/051647 mailed Feb. 19, 2013 (7 pages).
English translation of Japanese Office Action issued in counterpart Japanese Application No. 2013-557309 dated Feb. 7, 2014 (4 pages).
International Search Report issued in corresponding PCT Application No. PCT/JP2013/051647 mailed Feb. 19, 2013 (4 pages).
Written Opinion issued in corresponding PCT Application No. PCT/JP2013/051647 mailed Feb. 19, 2013 (5 pages).
Japanese Office Action issued in counterpart Japanese Application No. 2013-557309 dated Feb. 7, 2014 (4 pages).
Office Action in counterpart Chinese Application No. 201380071483.8 issued on Jan. 22, 2017 (14 pages).
Office Action issued in corresponding Canadian Application No. 2,902,300 dated Aug. 4, 2016 (4 pages).
Extended European Search Report issued in corresponding European Application No. 13873100.5 dated (7 pages).
Office Action issued in corresponding Canadian Application No. 2902300 dated Jun. 8, 2017 (3 pages).
Examination Report issued in corresponding European Application No. 13 873 100.5 dated Jul. 10, 2017 (5 pages).

* cited by examiner

DISTANCE MEASUREMENT SYSTEM AND DISTANCE MEASUREMENT METHOD

CROSS-REFERENCE TO RELATED APPLICATIONS

This is a national stage application under 35 U.S.C. 371 of International Patent Application No. PCT/JP2013/051647 filed Jan. 25, 2013, of which full contents are incorporated herein by reference.

BACKGROUND OF THE INVENTION

The present invention relates to a distance measuring system and a distance measuring method.

DESCRIPTION OF THE RELATED ART

A crack such as creep damage may occur in a weld (longitudinal welding line) of a large-diameter pipe used for a boiler and the like (for example, see Japanese Patent Application Laid-open Publication No. 2009-20075). In such a pipe and a weld, distortion which occurs in the pipe and the weld is measured, to grasp an indication of a crack in the pipe and repair timing and replacement timing (lifetime) of the pipe and the weld.

In general, it is necessary to measure distortion for a long time in a high-temperature state to obtain the repair timing and the like from distortion which occurs in a weld and the like. However, under the present situation, since there is no distortion sensor that is capable of measuring the distortion at high accuracy for a long time in the high-temperature state, it is difficult to accurately grasp an indication of occurrence of a crack in a pipe and a weld.

The present invention has been made in view of the above-mentioned problem and an object thereof is to provide a distance measuring system which can accurately grasp an indication of occurrence of a crack in a pipe and a weld.

SUMMARY OF THE INVENTION

A distance measuring system according to an aspect of the present invention includes: a reference member configured to be provided on a surface of a first pipe made of metal, the reference member serving as a reference for distance measurement; an attachment member provided on a surface of a second pipe, made of metal, connected with the first pipe through a weld; a distance sensor configured to be attached to the attachment member, to measure a distance to the reference member; and a measuring unit configured to measure the distance based on an output from the distance sensor.

Other features of the present invention will become apparent from descriptions of the present specification and of the accompanying drawings.

BRIEF DESCRIPTION OF THE DRAWINGS

For more thorough understanding of the present invention and advantages thereof, the following description should be read in conjunction with the accompanying drawings, in which.

DETAILED DESCRIPTION OF THE INVENTION

At least the following details will become apparent from descriptions of the present specification and of the accompanying drawings.

Figure 1:
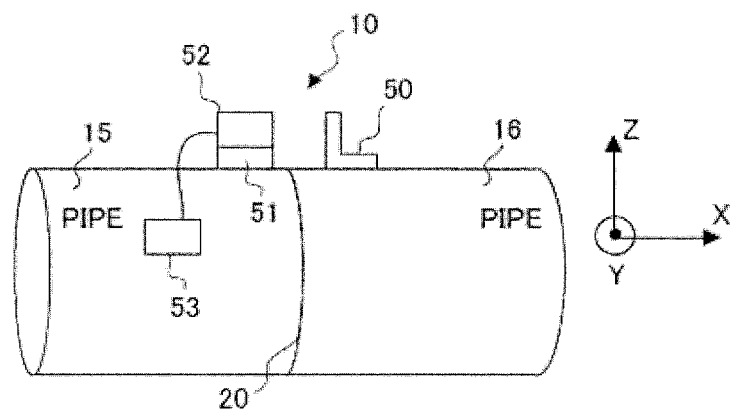
FIG. 1 is a diagram illustrating the outline of a distance measuring system 10.
Figure 2:
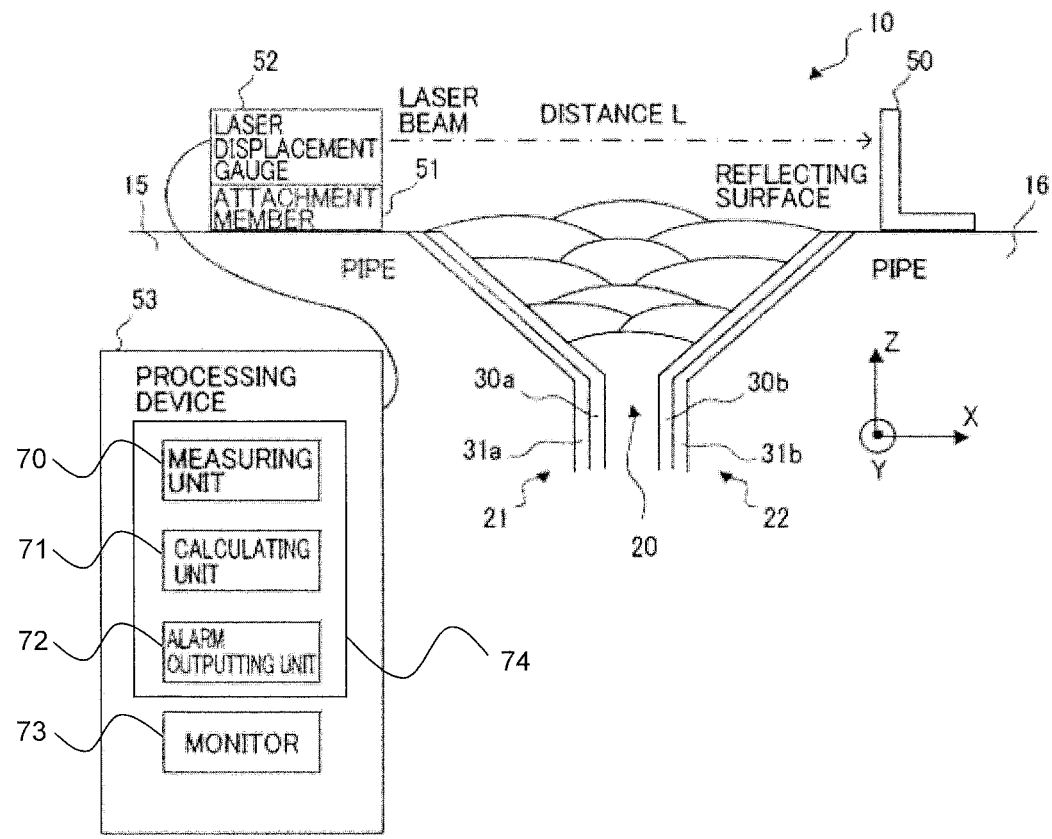
FIG. 2 is a diagram to describe the details of the distance measuring system 10.
Figure 3:
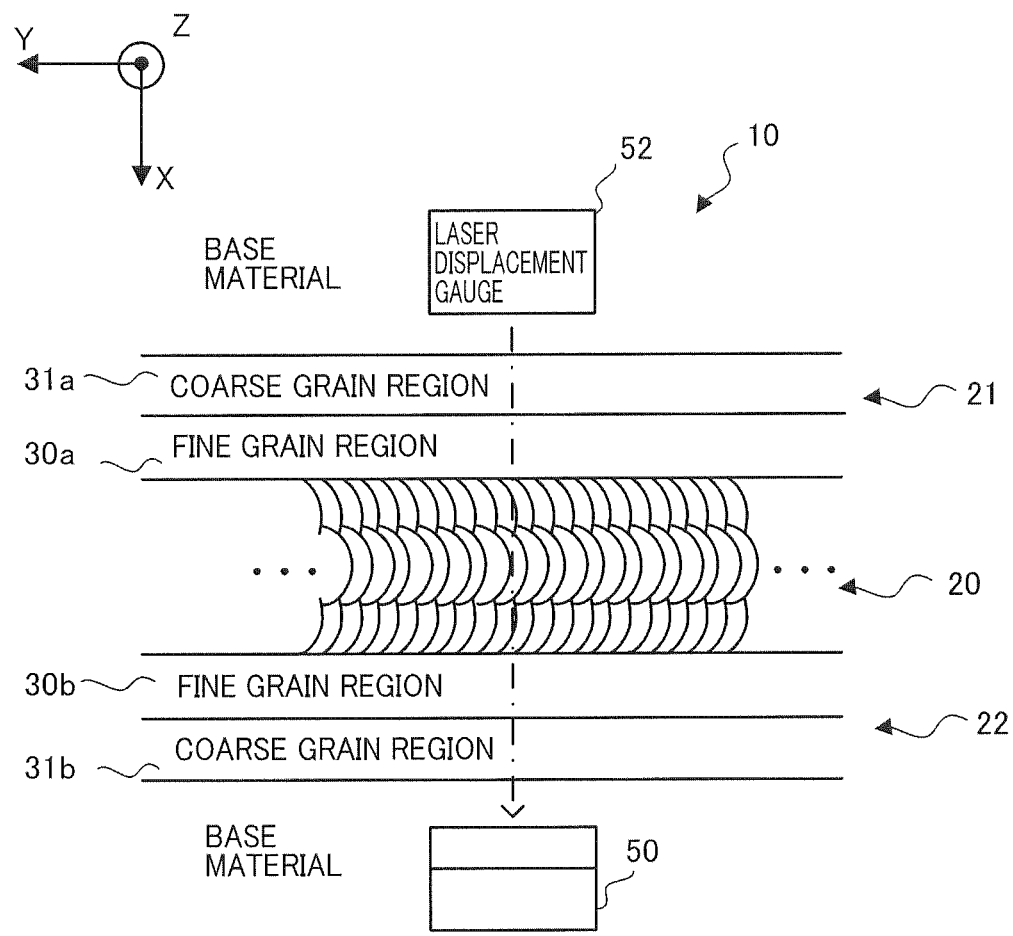
FIG. 3 is a plan view to describe the positional relationship between a reflecting plate 50 and a laser displacement gauge 52.

FIG. 1 is a diagram illustrating the outline of a distance measuring system 10 according to an embodiment of the present invention in which pipes 15 and 16 are provided, and FIG. 2 is a diagram to describe the details of the distance measuring system 10. Moreover, FIG. 3 is a plan view to describe the positional relationship between a reflecting plate 50 and a laser displacement gauge 52 in the distance measuring system 10. Here, in FIG. 2, a region in which the distance measuring system 10 is provided is magnified. Moreover, in each figure, the XY plane is a horizontal surface and the +Z axis direction is toward the upper side of the perpendicular direction.

The pipes 15 and 16 are large-diameter pipes made of stainless steel (metal) used for a boiler, and the opening part of one end of the pipe 15 and the opening part of one end of the pipe 16 are welded together (longitudinal welding). Note that respective other ends of the pipes 15 and 16 are connected with various devices or other pipes of the boiler, but they are omitted here for convenience.

Heat-affected zones 21 and 22 obtained by changing the structure of the pipes 15 and 16 (base materials) by heat at the time of welding are created in the pipes 15 and 16, respectively.

The heat-affected zone 21 includes a coarse grain region 30a and a fine grain region 31a formed with crystal grains that are finer than crystal grains forming the coarse grain region 30a. Note that the coarse grain region 30a is created on the side of a weld 20 to which the pipes 15 and 16 are welded.

Similarly to the heat-affected zone 21, the heat-affected zone 22 includes a coarse grain region 30b created on the weld 20 side and a fine grain region 31b. As such, the heat-affected zones 21 and 22 are created in regions on both sides of the weld 20.

In the welded pipes 15 and 16, when the boiler is operating and the pipes 15 and 16 are exposed to high temperature for a long time, distortion and creep damage occur in the weld 20 and the heat-affected zones 21 and 22. Further, for example, when distortion occurs, the weld 20 and the heat-affected zones 21 and 22 (especially, the fine grain regions 31a and 31b) expand in the longitudinal direction of the pipes 15 and 16. Note that the expansion having occurred in the weld 20 and the heat-affected zones 21 and 22 is maintained even in a state where the pipe 15 and the like are cold, that is, in a state where the boiler is stopped and the pipe 15 and the like are at substantially ordinary temperature.

<<Regarding Distance Measuring System 10>>

The distance measuring system 10 is a system to determine a change (expansion) in the distances between the weld 20 and the heat-affected zones 21 and 22, and includes the reflecting plate 50, an attachment member 51, the laser displacement gauge 52 and a processing device 53.

The reflecting plate 50 (reference member) is an L-shaped member which is used as a reference when the distance is measured. A bottom surface of the reflecting plate 50 welded to a substantially waterside surface of the pipe 16 (first pipe) and a reflecting surface bent so as to be vertical to the bottom surface are formed in the reflecting plate 50. Note that the reflecting plate 50 is superior in heat resistance and is made of an alloy (for example, an inconel (registered trademark) alloy), platinum or the like, which are less likely to be oxidized and deformed. Note that, in an embodiment of the present invention, a material of the reflecting plate 50 is selected such that the temperature, at which the oxidation of the material forming the reflecting plate 50 progresses, is sufficiently higher than the maximum value of the temperature of the pipes 15 and 16 (for example, 450° C. at which a creep phenomenon is assumed to occur).

Figure 4:
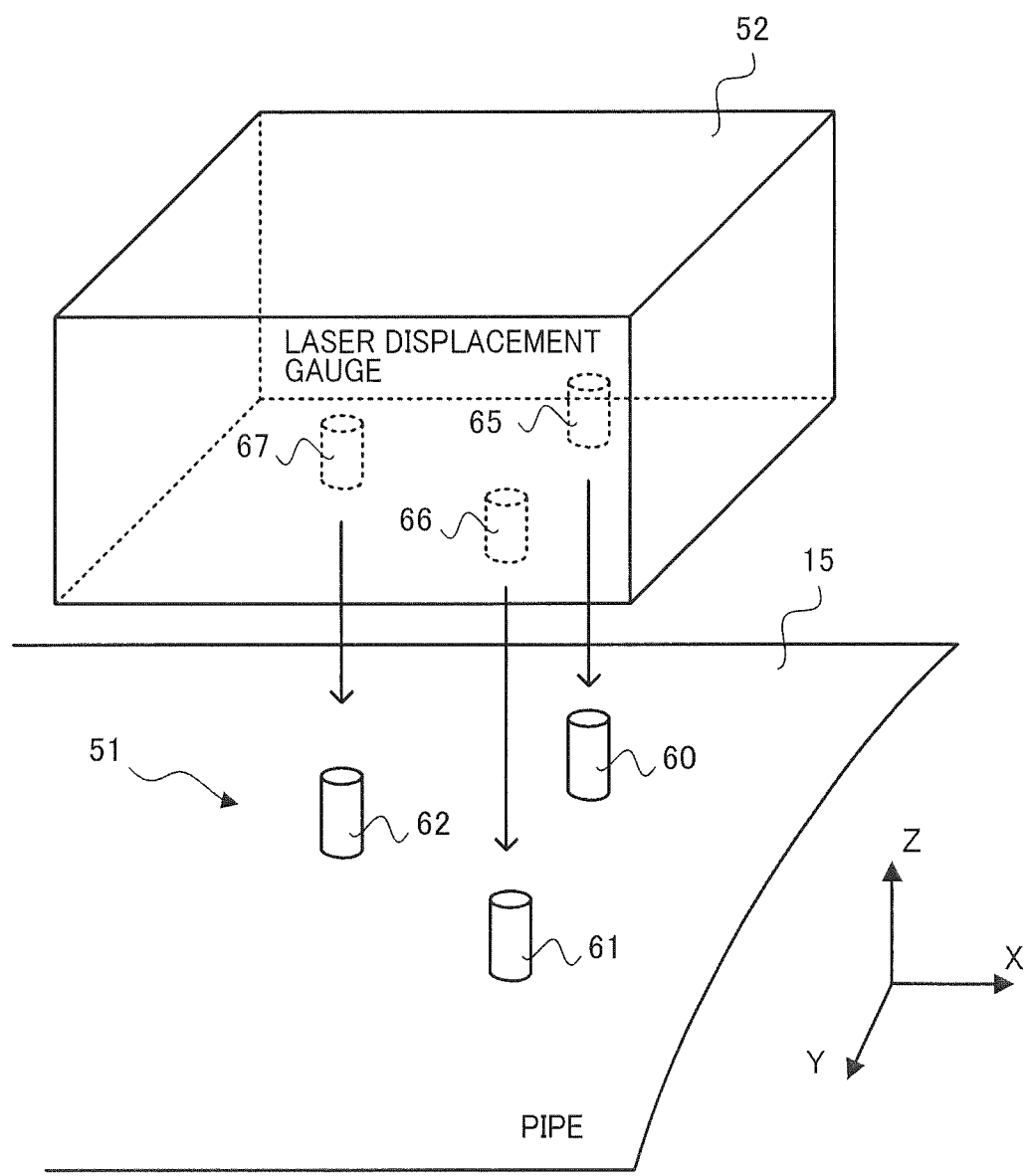
FIG. 4 is a diagram to describe the attachment and detachment of the laser displacement gauge 52.

The attachment member 51 is a member to which the laser displacement gauge 52 is attached, and includes three cylindrical pins 60 to 62, for example, as illustrated in FIG. 4. The pins 60 to 62 are pins to determine the attachment position of the laser displacement gauge 52 at high accuracy, and each bottom surface thereof is welded to a surface that is substantially waterside in the pipe 15 (second pipe). Moreover, when the laser displacement gauge 52 is attached, the pins 60 to 62 are welded to the positions at which the laser displacement gauge 52 and the reflecting surface of the reflecting plate 50 face to each other. The pins 60 to 62 and the reflecting plate 50 are welded to the surfaces of the pipes 15 and 16, across the weld 20 and the heat-affected zones 21 and 22, so as to be able to measure a change (expansion) in the distance between the weld 20 and the heat-affected zones 21 and 22. Note that, similarly to the reflecting plate 50, the attachment member 51 is superior in heat resistance and made of an alloy (for example, an inconel (registered trademark) alloy), platinum or the like, which are less likely to be oxidized and deformed. Note that, in the present embodiment, the material of the attachment member 51 is selected such that the temperature, at which the oxidation of a material forming the attachment member 51 progresses, is sufficiently higher than the maximum value of the temperature of the pipes 15 and 16 (for example, 450° C. at which a creep phenomenon is assumed to occur).

Figure 5:
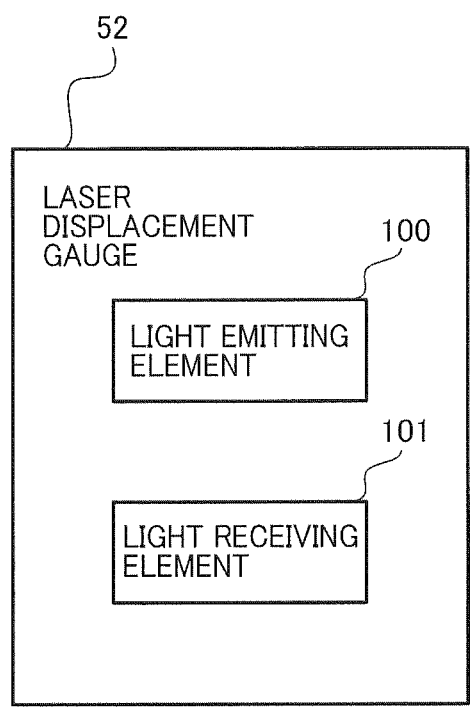
FIG. 5 is a diagram illustrating one example of the configuration of the laser displacement gauge 52.

The laser displacement gauge 52 is a laser-type (optical-type) distance sensor that is detachable with respect to the attachment member 51, and attachment holes 65 to 67 in which the pins 60 to 62 are inserted respectively are formed in the bottom surface of the laser displacement gauge 52. Moreover, as illustrated in FIG. 5, the laser displacement gauge 52 includes a light emitting element 100 and a light receiving element 101.

The light emitting element 100 is a semiconductor laser configured to output a laser beam to be radiated to the reflecting surface of the reflecting plate 50. The light receiving element 101 is configured to receive the laser beam reflected at the reflecting plate 50 and output a signal corresponding to a distance L from the laser displacement gauge 52 to the surface of the reflecting surface of the reflecting plate 50. Note that since the laser displacement gauge 52 uses the semiconductor laser, it is possible to measure the distance L only in a case where the ambient temperature is in a predetermined temperature range T (e.g., −10° C. to 45° C.), for example.

The processing device 53 is a device configured to perform various kinds of processing on the basis of an output from the laser displacement gauge 52, and includes a measuring unit 70, a calculating unit 71, an alarm outputting unit 72 and a monitor 73. Note that the measuring unit 70, the calculating unit 71 and the alarm outputting unit 72 are functional blocks to be implemented by a microcomputer 74 included in the processing device 53.

The measuring unit 70 is configured to measure (calculate) the distance L on the basis of the output from the laser displacement gauge 52. The calculating unit 71 is configured to calculate the remaining life of the pipe 15 and the like on the basis of the measured distance L and information indicative of the relationship between the distance L and the remaining lives of the pipes 15 and 16 and the weld 20, which are stored beforehand in a memory (not illustrated) of the processing device 53. Note that the relationship between the distance L and the remaining lives of the pipe 15 and the like is experimentally obtained beforehand.

The alarm outputting unit 72 is configured to display an alarm on the monitor 73 when the calculated remaining lives of the pipe 15 and the like have become shorter than a predetermined level. Thus, a worker can immediately determine that a crack has occurred in the pipe 15 and the like and the remaining life thereof has been shortened.

<<Processing of measuring distance L>>

Figure 6:
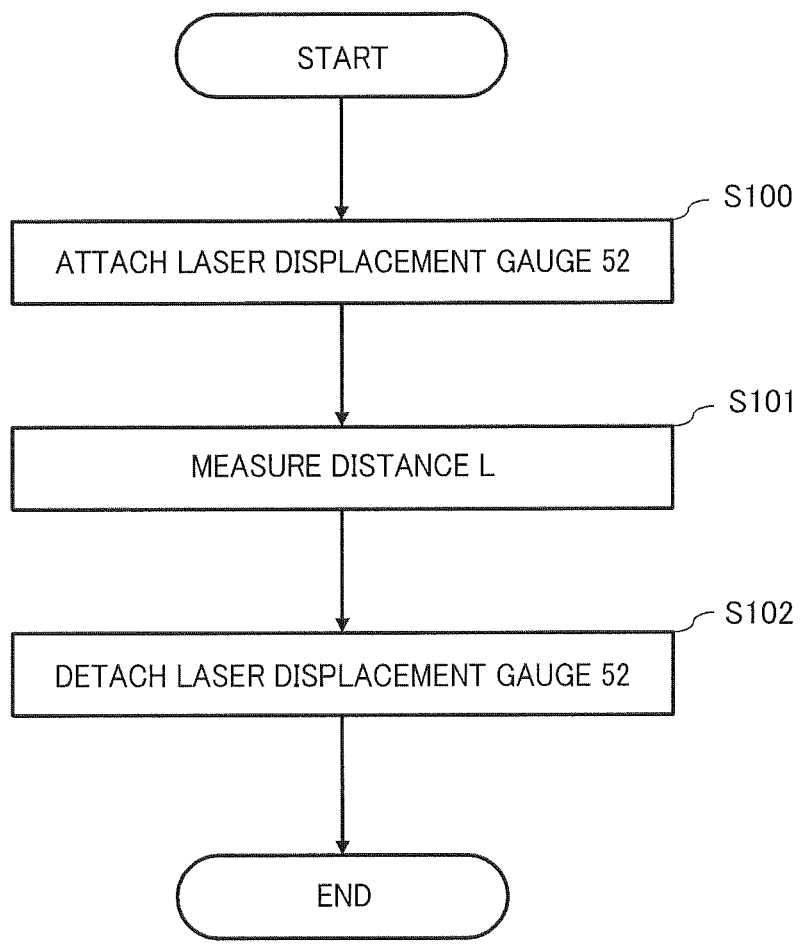
FIG. 6 is a flowchart illustrating one example of a process to be performed by a worker when a distance L is measured.

Here, processing which is performed by a worker when the distance L is measured using the distance measuring system 10 is described with reference to FIG. 6. As mentioned above, the laser displacement gauge 52 is capable of measuring the distance L only in a case where it is in the predetermined temperature range T. Thus, during operation while a boiler is operating (when the temperature of the pipe 15 rises very high), the laser displacement gauge 52 is detached. Further, for example, the worker measures the distance L during a periodic inspection when the boiler is stopped. Note that the periodic inspection is conducted, for example, every year.

First, at the time of the periodic inspection, that is, in a case where the temperature of the pipe 15 and the like are substantially at an ordinary temperature (for example, 25° C.) and is in the predetermined temperature range T, the worker attaches the laser displacement gauge 52 to the attachment member 51 (S100). Then, the worker operates the laser displacement gauge 52 and measures the distance L (S101). When the remaining lives of the pipe 15 and the like are calculated in addition to the distance L, the worker detaches the laser displacement gauge 52 (S102). Since such processing is repeated every periodic inspection, the worker can accurately obtain the distance L (distortion) indicative of a sign of occurrence of a crack that occurs in the pipe 15 and the like, every periodic inspection.

Hereinabove, the distance measuring system 10 according to an embodiment of the present invention has been described above. The worker can grasp a change in the distance L by using the distance measuring system 10. Moreover, the distance L changes according to the state of a crack that occurs in the weld 20. Thus, the worker can accurately grasp an indication of occurrence of a crack in the weld 20 and the pipe 15 and the like on the basis of the change in the distance L. Moreover, since accurate timing to repair/replace the pipe 15 can be determined on the basis of such information, it is possible to reduce useless repairs and reduce maintenance costs.

Moreover, it is assumed in the present embodiment, that the reflecting plate 50 is welded to the pipe 16, but it is not limited to this. For example, a member similar to the attachment member 51 may be provided on the surface of the pipe 16, and the reflecting plate 50 may be attached as needed. However, in a case where the reflecting plate 50 is welded to the pipe 16, an error at the time of attaching the reflecting plate 50 can be eliminated, and thus it is possible to measure the distance L more accurately.

Moreover, in the present embodiment, a material of the reflecting plate 50 is selected such that the temperature, at which the oxidation of the material forming the reflecting plate 50 progresses, becomes sufficiently higher than the maximum temperature of the pipes 15 and 16. Thus, it is possible to prevent the reflecting plate 50 from being oxidized and the measurement accuracy of the distance L from deteriorating.

Moreover, in the present embodiment, a material of the attachment member 51 is selected such that the temperature, at which the oxidation of the material forming the attachment member 51 progresses, becomes sufficiently higher than the maximum value of the temperature of the pipes 15 and 16. Thus, it is possible to prevent the attachment member 51 from being oxidized and the measurement accuracy of the distance L from deteriorating.

Moreover, a capacitance-type sensor or the like may be used as a distance sensor, but it is possible to measure the distance L more accurately by using the laser displacement gauge 52.

Moreover, the distance measuring system 10 measures the distance L of regions across longitudinal welding, but, for example, the distance across a weld when two pipes are welded in a T-shape may be measured. Even in such a case, an effect similar to that in the present embodiment can be obtained.

Moreover, a worker can attach and detach the laser displacement gauge 52 with respect to the pins 60 to 62 at appropriate timing.

Moreover, the laser displacement gauge 52 is attached to the pipe 16 at the time of periodic inspection, and the distance L is measured. Thus, the laser displacement gauge 52 can accurately measure the distance L.

When a crack or the like occurs in the pipe 15 or the like, especially the areas of the fine grain regions 31a and 31b expand. Since the reflecting plate 50 and the attachment member 51 are provided across the weld 20 and the heat-affected zones 21 and 22, it becomes possible to accurately grasp the influence of the crack.

Note that the above-mentioned embodiment is provided to facilitate the understanding of the present invention, and it is not provided to limit the understanding of the present invention. The present invention may be changed and improved without departing from the gist thereof, and the equivalent thereof may be included in the present invention.

What is claimed is:

1. A distance measuring system comprising:
    a reflecting plate that reflects a laser beam, wherein
        the reflecting plate is welded to a surface of a first pipe,
        the first pipe is connected to a second pipe through a weld,
        the first and the second pipes are made of metal,
        the reflecting plate is made of a material whose oxidation progresses at a temperature sufficiently higher than a maximum temperature of the first and the second pipes when the first and the second pipes are heated, and
        the reflecting plate serves as a reference for distance measurement;
    a plurality of pins provided on a surface of the second pipe;
    laser displacement gauge attached to the plurality of pins, and that radiates the laser beam to the reflecting plate and outputs a signal indicative of a distance to the reflecting plate based on the reflected laser beam; and
    processing device including a microcomputer that measures the distance based on the signal output from the laser displacement gauge.

2. The distance measuring system according to claim 1, wherein
    the weld welds together an opening part of one end of the first pipe and an opening part of one end of the second pipe.

3. The distance measuring system according to claim 1, wherein
    the laser displacement gauge is detachably attached to the plurality of pins.

4. The distance measuring system according to claim 1, wherein
    the reflecting plate and the plurality of pins are provided on respective surfaces of the first and the second pipes across the weld and a heat-affected zone, wherein the heat-affected zone is created on both sides of the weld when the first and the second pipes are welded together.

5. The distance measuring system according to claim 1, wherein maximum temperature of the first and the second pipes is 450° C.

6. The distance measuring system according to claim 1, wherein
    the plurality of pins are made of a material whose oxidation progresses at a temperature sufficiently higher than the maximum temperature of the first and the second pipes when the first and the second pipes are heated.

7. The distance measuring system according to claim 6, wherein
    the laser displacement gauge becomes attached to the plurality of pins when a temperature of the second pipe is within a predetermined temperature range in which the laser displacement gauge can measure the distance to the reflecting plate.

8. A distance measuring method comprising:
    radiating, with a laser displacement gauge, a laser beam to a reflecting plate that is welded to a surface of a first pipe and that serves as a reference for distance measurement, wherein
        the first pipe is connected to a second pipe through a weld,
        a plurality of pins are provided on a surface of the second pipe and are attached to the laser displacement gauge,
        the reflecting plate is made of a material whose oxidation progresses at a temperature sufficiently higher than a maximum temperature of the first and the second pipes when the first and the second pipes are heated, and
        the first and the second pipes are made of metal;
    reflecting the laser beam with the reflecting plate;
    outputting a signal indicative of a distance from the laser displacement gauge to the reflecting plate based on the reflected laser beam; and
    measuring the distance based on the signal output from the laser displacement gauge.

9. The distance measuring method according to claim 8, wherein maximum temperature of the first and the second pipes is 450° C.

* * * * *